(12) United States Patent
Sarkar et al.

(10) Patent No.: US 8,945,917 B2
(45) Date of Patent: Feb. 3, 2015

(54) ENHANCED SURFACE AREA CONICO-CYLINDRICAL FLASK (ES-CCF) FOR BIOFILM CULTIVATION

(75) Inventors: Sreyashi Sarkar, Kolkata (IN); Debashis Roy, Kolkata (IN); Joydeep Mukherjee, Kolkata (IN)

(73) Assignee: Counci of Scientific & Industrial Research and School of Environmental Studies, New Delhi (IN)

( * ) Notice: Subject to any disclaimer, the term of this patent is extended or adjusted under 35 U.S.C. 154(b) by 683 days.

(21) Appl. No.: 13/111,022

(22) Filed: May 19, 2011

(65) Prior Publication Data

US 2012/0295293 A1    Nov. 22, 2012

(51) Int. Cl.
*C12M 1/00* (2006.01)
*C12Q 1/37* (2006.01)
*B01L 3/08* (2006.01)
(Continued)

(52) U.S. Cl.
CPC *B01L 3/08* (2013.01); *C12M 23/08* (2013.01); *C12M 23/34* (2013.01); *C12M 25/06* (2013.01); *G01N 2333/948* (2013.01); *B01L 2200/0684* (2013.01); *B01L 2300/0858* (2013.01)
USPC ....... 435/304.1; 435/23; 435/299.1; 366/233; 215/382; 215/386

(58) Field of Classification Search
CPC ...... C12M 23/08; C12M 25/06; C12M 23/34; B01L 3/08; B01L 2300/0858; B01L 2200/0684
USPC ...................... 435/304.1, 299.1, 23; 366/233; 215/382, 386
See application file for complete search history.

(56) References Cited

U.S. PATENT DOCUMENTS 4,912,058 A * 3/1990 Mussi et al. ............... 435/299.2
5,084,393 A * 1/1992 Rogalsky .................. 435/299.2
(Continued)

FOREIGN PATENT DOCUMENTS

EP        0765934    *    4/1997    ............... C12M 1/24

OTHER PUBLICATIONS

Ahimou, F., Semmens, M.J., Haugstad, G., Novak, P.J., 2007. Effect of protein, polysaccharide, and oxygen concentration profiles on biofilm cohesiveness. Appl. Environ. Microbiol. 73, 2905-2910.
(Continued)

*Primary Examiner* — Michael Marcheschi
*Assistant Examiner* — Danielle Henkel
(74) *Attorney, Agent, or Firm* — Edwards Wildman Palmer LLP; Barry Kramer; Daniel J. Fiorello

(57) ABSTRACT

A novel enhanced surface area conico-cylindrical flask (ES-CCF) providing increased surface area by virtue of its' inner arrangement and useful in routine small-scale studies of bio-actives production by any biofilm-forming marine as well as terrestrial microorganisms. Compared to corresponding Erlenmeyer flask of similar volume the ES-CCF provides more than 80% additional surface for biofilm attachment and growth. The ES-CCF does not require steam sterilization and is durable as the device is constructed of polymethyl methacrylate or any other such hydrophobic material and offers possibility of altering the nature of the growth surface (hydrophilic and hydrophobic). The ES-CCF also provides external aeration like a bioreactor, thus increasing the versatility of applications. Further, the device can be operated as a cylindrical flask, that is without the inner arrangement.

9 Claims, 6 Drawing Sheets

(51) Int. Cl.
*C12M 1/24* (2006.01)
*C12M 1/12* (2006.01)

(56) References Cited

U.S. PATENT DOCUMENTS

2004/0191895 A1* 9/2004 Whitley ............... 435/299.2
2009/0298163 A1* 12/2009 Bennett et al. ......... 435/294.1

OTHER PUBLICATIONS

Atlas, R.M., 2005. Handbook of Media for Environmental Microbiology, Second Ed. Taylor Francis, Boca Raton.
Bruhn, J.B., Gram, L., Belas, R., 2007. Production of antibacterial compounds and biofilm formation by *Roseobacter* species are influenced by culture conditions. Appl. Environ. Microbiol. 73, 442-450.
Gupta, A., Joseph, B., Mani, A., Thomas, G., 2008. Biosynthesis and properties of an extracellular thermostable serine alkaline protease from *Virgibacillus pantothenticus*. World J. Microbiol. Biotechnol. 24, 237-243.
Iijima, S., Washio, K., Okahara, R., Morikawa, M., 2009. Biofilm formation and proteolytic activities of *Pseudoalteromonas* bacteria that were isolated from fish farm sediments. Microb. Biotechnol. 2, 361-369.
Kruger, N.J., 1994. Bradford method for protein quantification. In: Walker, J.M. (Ed.), Basic Protein and Peptide Protocols. Springer Verlag, New York, pp. 9-15.
Penesyan, A., Kjelleberg, S., Egan, S., 2010. Development of novel drugs from marine surface associated microorganisms. Mar. Drugs. 8, 438-459.
Rodrigues, C., Bhosle, N.B., 1991. Exopolysaccharide production by *Vibrio fischeri*, a fouling marine bacterium. Biofouling 4, 301-308.
Sana, B., Ghosh, D., Saha, M., Mukherjee, J., 2006. Purification and characterization of a salt, solvent, detergent and bleach tolerant protease from a new gamm—Proteobacterium isolated from the marine environment of the Sundarbans. Process Biochem. 41, 208-215.
Saravanan, P. and Jayachandran, S., 2008. Preliminary characterization of exopolysaccharides produced by a marine biofilm-forming bacterium *Pseudoalteromonas ruthenica* (SBT 033). Lett. Appl. Microbiol. 46, 1-6.

Sarkar, S., Mukherjee, J., Roy, D., 2009. Antibiotic production by a marine isolate (MS310) in an ultra-low-speed rotating disk bioreactor. Biotechnol. Bioprocess Eng. 14, 775-780.
Sarkar, S., Roy, D., Mukherjee, J., 2010. Production of a potentially novel antimicrobial compound by a biofilm-forming marine *Streptomyces* sp. in a niche-mimic rotating disk bioreactor. Bioprocess Biosyst. Eng. 33, 207-217.
Sarkar, S., Saha, M., Roy, D., Jaisankar, P., Das, S., Roy, L.G., Gachhui, R., Sen, T., Mukherjee, J., 2008. Enhanced production of antimicrobial compounds by three salt-tolerant actinobacterial strains isolated from the Sundarbans in a niche-mimic bioreactor. Mar. Biotechnol. 10, 518-526.
Yan, L., Boyd, K.G., Adams, D.R., Burgess, J.G., 2003. Biofilm-specific cross-species induction of antimicrobial compounds in Bacilli. Appl. Environ. Microbiol. 69, 3719-3727.
Yan, L., Boyd, K.G., Burgess, J.G., 2002. Surface attachment induced production of antimicrobial compounds by marine epiphytic bacteria using modified roller bottle cultivation. Mar. Biotechnol. 4, 356-366.
Villena et al., "Production of Cellulase by *Aspergillus niger* biofilms Developed on Polyester Cloth," Letters in Applied Microbiology 43 (2006) pp. 262-268.
Villena et al. "Morphological Patterns of *Aspergillus niger* biofilms and pellets related to lignocellulolytic enzyme productivities," Letters in Applied Microbiology 45 (2007) pp. 231-237.
Martinez et al., "*Cryptococcus neoformans* Biofilm Formation Depends on Surface Support and Carbon Source and Reduces Fungal Cell Susceptibility to Heat, Cold, and UV Light," Appl. Environ. Microbiol. 2007; 73(14); 4592-4601.
Jayaraman et al. "Characterization of axenic *Pseudomonas Fragi* and *Escherichia coli* biofilms that inhibit corrosion of SAE 1018 steel," Journal of Applied Microbiology 84 (1998), pp. 485-492.
Sarkar et al. "Enhanced Protease Production in a polymethylmethacrylate conico-cylindrical flask by two biofilm-forming bacteria," Bioresourcce Technology 102(2011) pp. 1849-1855.
Mitra et al. "A novel conico-cylindrical flask aids easy identification of critical process parameters for cultivation of marine bacteria," Appl. Microbiol. Biotechnol. (2011) 90: 321-330.

* cited by examiner a b c a b c

ENHANCED SURFACE AREA CONICO-CYLINDRICAL FLASK (ES-CCF) FOR BIOFILM CULTIVATION

FIELD OF THE INVENTION

The present invention relates to a novel enhanced surface area conico-cylindrical flask (ES-CCF), useful in routine small-scale studies. More particularly, the present invention relates to a device for obtaining metabolites (e.g. proteases, esterases etc.) from any biofilm-forming microorganisms both marine and terrestrial that produce desired products at highest rates when attached to surfaces. The present invention provides enhanced surface area by virtue of its novel inner arrangement.

BACKGROUND OF THE INVENTION

Surface attachment and biofilm formation are known to influence metabolite and enzyme production by microorganisms (Iijima, S., Washio, K., Okahara, R., Morikawa, M., 2009. Biofilm formation and proteolytic activities of *Pseudoalteromonas* bacteria that were isolated from fish farm sediments. Microb. Biotechnol. 2, 361-369; Penesyan, A., Kjelleberg, S., Egan, S., 2010. Development of novel drugs from marine surface associated microorganisms. Mar. Drugs. 8, 438-459) and specialized reactors are required for organisms that produce desired products at highest rates when attached to surfaces. Such microorganisms can be cultured in modified roller bottles (Yan, L., Boyd, K. G., Burgess, J. G., 2002. Surface attachment induced production of antimicrobial compounds by marine epiphytic bacteria using modified roller bottle cultivation. Mar. Biotechnol. 4, 356-366), air-membrane surface (AMS) bioreactors (Yan, L., Boyd, K. G., Adams, D. R., Burgess, J. G., 2003. Biofilm-specific cross-species induction of antimicrobial compounds in Bacilli. Appl. Environ. Microbiol. 69, 3719-3727) or in rotating disc bioreactors (RDBR) (Sarkar, S., Saha, M., Roy, D., Jaisankar, P., Das, S., Roy, L. G., Gachhui, R., Sen, T., Mukherjee, J., 2008. Enhanced production of antimicrobial compounds by three salt-tolerant actinobacterial strains isolated from the Sundarbans in a niche-mimic bioreactor. Mar. Biotechnol. 10, 518-526; Sarkar, S., Mukherjee, J., Roy, D., 2009. Antibiotic production by a marine isolate (MS310) in an ultra-low-speed rotating disk bioreactor. Biotechnol. Bioprocess Eng. 14, 775-780; Sarkar, S., Roy, D., Mukherjee, J., 2010. Production of a potentially novel antimicrobial compound by a biofilm-forming marine *Streptomyces* sp. in a niche-mimic rotating disk bioreactor. Bioprocess Biosyst. Eng. 33, 207-217) that allow growth as biofilms in contact with air. Investigations by Yan et al., 2002, indicated that biofilm-forming bacteria produce important metabolites under surface attached conditions. The modified roller bottle cultivation can be used to increase production of important metabolites (Yan et al., 2002). Another new configuration, the air-membrane surface (AMS) bioreactor, designed by Yan et al., 2003, allowed bacteria to grow as a surface-attached bio-film in contact with air. Results obtained showed that specific molecules are produced only when the producer microbes can grow as biofilms. Several studies were conducted in the niche-mimic rotating disc bioreactor (RDBR) that mimicked the intertidal habitat of three estuarine isolates, supported bio-film formation as well as production of antimicrobial metabolites, in particular, actinomycin D (Sarkar et al., 2008, 2009, 2010).

Currently, there are no small-scale vessels that provide a high surface area and surface properties that favor attachment of biofilm-forming microbes.

OBJECTS OF THE INVENTION

The main object of the present invention is to provide a novel enhanced surface area conico-cylindrical flask (ES-CCF) for cultivation of any bio-film forming microorganism.

Another object of the present invention is to provide enhanced surface area by virtue of its inner arrangement.

Yet another object of the present invention is to provide a novel enhanced surface area conico-cylindrical flask (ES-CCF) constructed of polymethylmethacrylate (PMMA) or any other such hydrophobic material and not glass.

Still another object of the present invention is to provide an enhanced surface area conico-cylindrical flask (ES-CCF) that can be conveniently fitted into standard rotary shaker platforms.

Still another object of the present invention is to provide an enhanced surface area conico-cylindrical flask (ES-CCF) that allows external aeration like a bioreactor.

One another object of the present invention is to provide a low cost novel enhanced surface area conico-cylindrical flask (ES-CCF) that offers possibility of altering the nature of the growth surface (hydrophilic and hydrophobic).

One another object of the present invention is to provide a cylindrical flask (CF) that is an ES-CCF without the inner arrangement.

SUMMARY OF THE INVENTION

Accordingly, the present invention provides a novel enhanced surface area conico-cylindrical flask (ES-CCF) for biofilm cultivation comprising in combination, a lower cylindrical portion (11) closed at the lower end and covered by a funnel portion (5) at its upper end, a middle threading portion (6) joining the lower end of the said funnel portion and the upper end of the lower cylindrical portion, a neck (4) being mounted on the top of the said funnel portion, a screw cap (3) having two ports (1 and 2) for air inlet and air exhaust being detachably fitted in to the said neck; wherein the said flask is characterized in that the said lower cylindrical portion having an inner arrangement (7) to place plurality of equally spaced rectangular strips (8, 9, 10) mounted on a circular disk (12) placed at the lower end of the said flask.

In an embodiment of the present invention, the lower cylindrical portion and upper funnel portion of the flask are joined by screwing the upper part into the lower part.

In another embodiment of the present invention, the dimensions of the flask are: lower cylindrical portion (height, 150 mm; outer diameter, 80 mm; thickness, 5 mm); (b) upper funnel portion (diameter of the funnel base, 90 mm; diameter of funnel top, 40 mm).

In yet another embodiment of the present invention, the ports on the screw cap of the ES-CCF and CF are available for air inlet and exhaust (diameter of each port, 10 mm; diameter of the screw cap, 34 mm).

In yet another embodiment of the present invention, the flask provides enhanced surface area by virtue of its inner arrangement comprising of eight equally spaced rectangular strips mounted on a circular disk (height of the strip, 150 mm; thickness, 5 mm; diameter of the disk, 70 mm; thickness, 5 mm).

In still another embodiment of the present invention, the flask is made up of polymethylmethacrylate (PMMA) or any other hydrophobic material such as Teflon (DuPont), various plastics, hydrophobic latex, and silicone.

In another embodiment of the present invention, the use of PMMA leads to 202% and 22% enhancement in protease production by marine *Pseudomonas* sp. MTCC 8054 and *Virgibacillus pantothenticus* MTCC 6729 respectively.

In another embodiment of the present invention, the use of PMMA leads to 19,275% and 940% enhancement in growth of marine *Pseudomonas* sp. MTCC 8054 and *Virgibacillus pantothenticus* MTCC 6729 respectively.

In still another embodiment of the present invention, the flask allows external aeration like a bioreactor.

In still another embodiment of the present invention, the flask offers possibility of altering the nature of the growth surface of the inner arrangement (hydrophilic and hydrophobic).

In still another embodiment of the present invention, the flask is used for obtaining metabolites from any biofilm-forming microorganisms both marine and terrestrial.

In still another embodiment of the present invention, the flask is conveniently fitted into rotary shaker platforms.

In still another embodiment of the present invention, the flask provides enhanced surface area by virtue of its inner arrangement.

In still another embodiment of the present invention, the flask provides more than 80% additional surface for biofilm attachment and growth, compared to similar volume Erlenmeyer flask.

In yet another embodiment of the present invention, the flask does not require steam sterilization.

In still other embodiment of the present invention, the flask is durable as it is constructed of PMMA or any other such hydrophobic material selected from the group Teflon (DuPont), various plastics, hydrophobic latex, and silicone and not glass.

In an embodiment of the present invention, a method for obtaining metabolites from any biofilm-forming microorganisms both marine and terrestrial, utilizing the device ES-CCF, wherein the method comprises the steps of:
 a) cultivating marine *Pseudomonas* sp. MTCC 8054 and *Virgibacillus pantothenticus* MTCC 6729 in the novel enhanced surface area conico-cylindrical flask (ES-CCF) to obtain a culture suspension;
 b) assaying the activity of protease in the culture suspension as produced in step (a);
 c) simultaneously measuring the planktonic growth in the samples withdrawn from the suspension as obtained in step (a);
 d) simultaneously measuring the amount of biofilm formation by scraping an area of the ES-CCF as obtained from the culture suspension of step (a);
 e) simultaneously estimating the exopolysaccharide from the suspension as obtained in step (a);
 f) simultaneously determining the amount of soluble protein in the culture suspension of step (a).

In another embodiment of the present invention, the protease activity increases in the range from 848±22 U/mL to 1222.5±68 U/mL for marine *Pseudomonas* sp. MTCC 8054 and from 14.95±0.6 U/mL to 21.5±0.5 U/mL for *Virgibacillus pantothenticus* MTCC 6729.

In yet another embodiment of the present invention, the planktonic growth increases in the range from 0.0359±0.002 (DCW g/mL) to 0.0436±0.003 (DCW g/mL) for marine *Pseudomonas* sp. MTCC 8054 and from 0.072±0.03 (DCW g/mL) to 0.32±0.01 (DCW g/mL) for *Virgibacillus pantothenticus* MTCC 6729.

In yet another embodiment of the present invention the biofilm formation increases in the range from 0 to 0.0320±0.0010 g for marine *Pseudomonas* sp. MTCC 8054 and from 0 to 0.3729±0.0300 g for *Virgibacillus pantothenticus* MTCC 6729.

In yet another embodiment of the present invention, the exopolysaccharide increases in the range from 6.67±0.7 (µg/mL) to 19.47±2 (µg/mL) for marine *Pseudomonas* sp. MTCC 8054 and from 4.21±0.8 (µg/mL) to 26.32±0.8 (µg/mL) for *Virgibacillus pantothenticus* MTCC 6729.

In still another embodiment of the present invention, the increase in protease activity is in the range from 1.4 to 1.5 folds.

In still another embodiment of the present invention, the planktonic growth increases in the range from 1.2 to 4.4 folds.

In still another embodiment of the present invention, the biofilm formation increases by 0.0320±0.0010 g for marine *Pseudomonas* sp. MTCC 8054 and by 0.3729±0.0300 g for *Virgibacillus pantothenticus* MTCC 6729.

In still another embodiment of the present invention, the exopolysaccharide increases in the range from 2.9 to 6.25 folds.

BRIEF DESCRIPTION OF THE DRAWINGS

The present invention is illustrated in FIGS. 1 to 6 of the drawings accompanying this specification.

(b) Top view of inner arrangement with cylindrical base of the enhanced surface area conico-cylindrical flask (ES-CCF).

Figure 1:
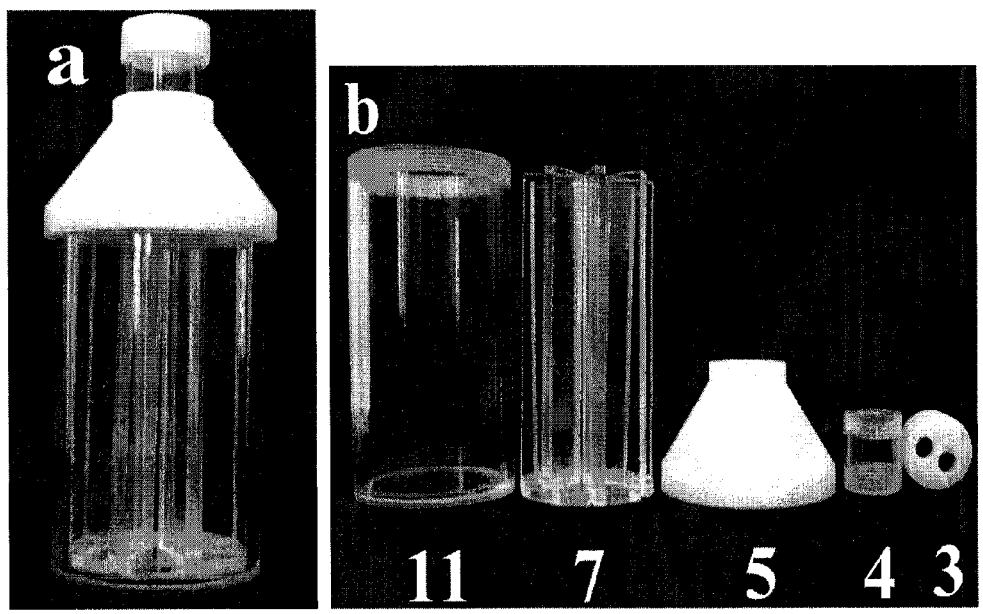
FIG. 1: (a) Enhanced surface area conico-cylindrical flask (ES-CCF); and (b) components of the ES-CCF, 11: lower cylindrical portion, 7: inner arrangement, 5: upper funnel portion, 4: neck for joining screw cap, 3: screw cap with provision for aeration.
Figure 2:
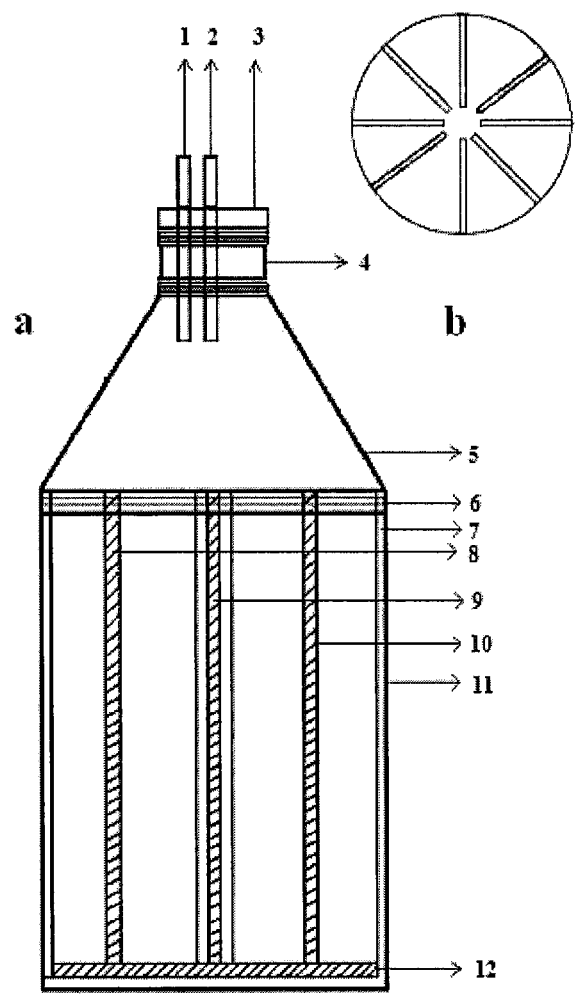
FIG. 2: (a) Schematic of the present device called the 'enhanced surface area conico-cylindrical flask (ES-CCF)'. Details of the individual parts are:
 1—Port for air in (diameter 10 mm) made up of polymethylmethacrylate (PMMA).
 2—Port for air out (diameter 10 mm) made up of polymethylmethacrylate (PMMA).
 3—Screw cap (diameter of the screw cap, 34 mm) made up of polypropylene.
 4—Neck
 5—Funnel portion (diameter of the funnel base, 90 mm; diameter of funnel top, 40 mm) made up of polypropylene.
 6—Threading
 7—Inner arrangement: The inner arrangement consisted of eight equally spaced rectangular strips mounted on a circular disk (height of the strip, 150 mm; thickness, 5 mm; diameter of the disk, 70 mm; thickness, 5 mm) made up of polymethylmethacrylate (PMMA) or any other such hydrophobic material. The surface area of the inner arrangement is 706.4 cm$^2$.
 8, 9, 10—Rectangular strips of inner arrangement
 11—Lower cylindrical portion (height, 150 mm; outer diameter, 80 mm; thickness, 5 mm) made up of polymethylmethacrylate (PMMA) or any other such hydrophobic material.
 12—Circular disk (diameter of the disk, 70 mm; thickness, 5 mm) made up of polymethylmethacrylate (PMMA) or any other such hydrophobic material.
Figure 3:
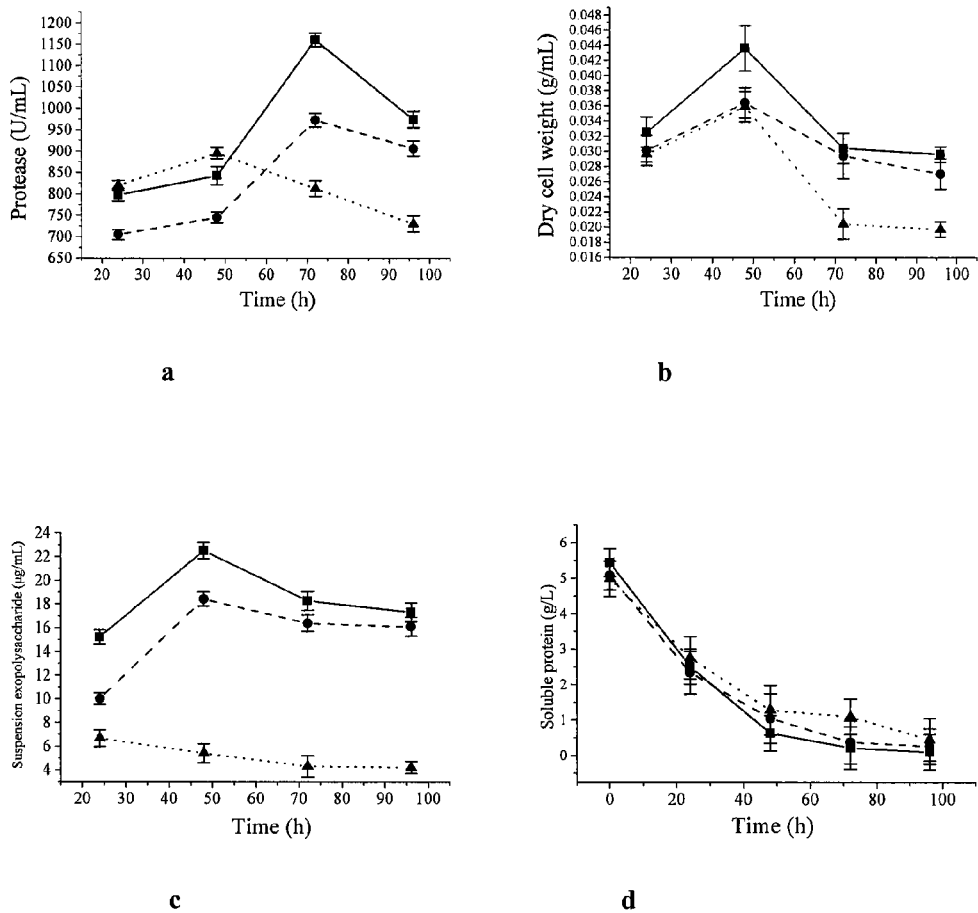

FIG. 3: Effect of flask configuration on (a) protease activity (b) dry cell weight (c) suspension exopolysaccharide and (d) medium soluble protein during cultivation of marine *Pseudomonas* sp. MTCC 8054. Symbols represent: ■

Enhanced surface area conico-cylindrical flask (ES-CCF); ●
Cylindrical flask (CF); ▲ Erlenmeyer flask (EF). Error bars
represent standard deviation of six determinations.

Figure 4:
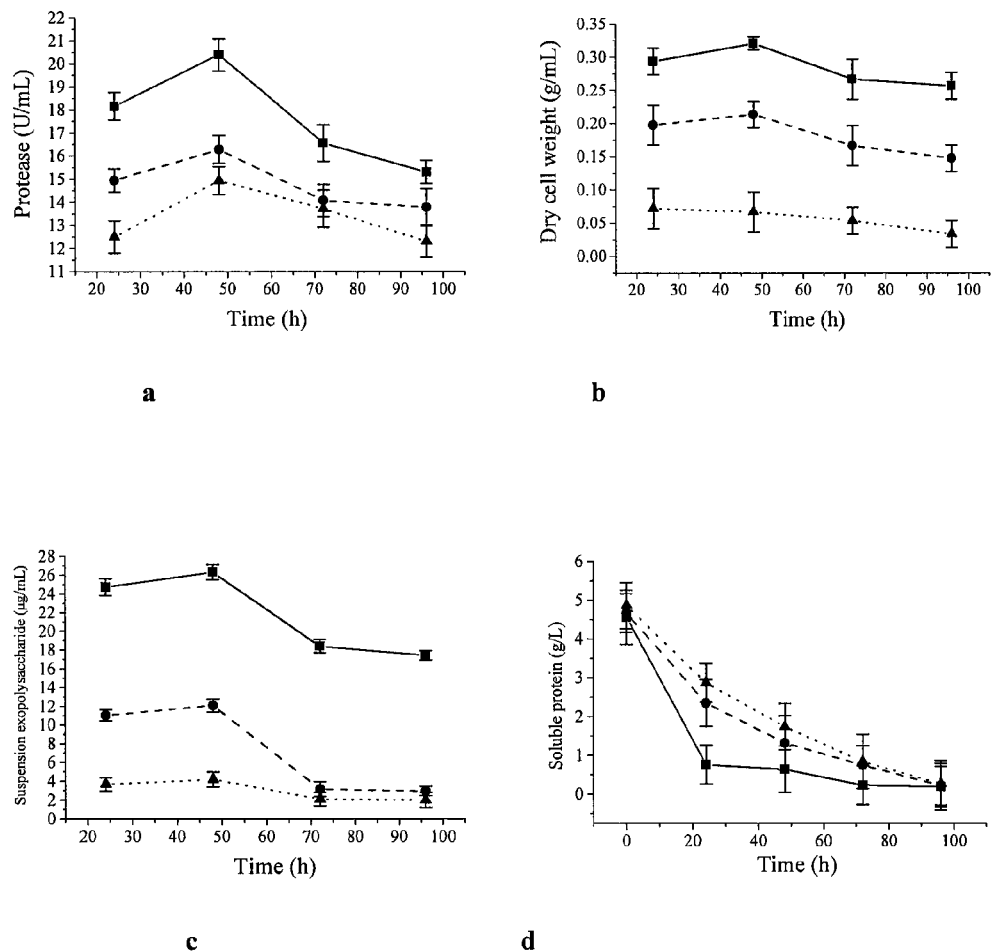

FIG. 4: Effect of flask configuration on (a) protease activity (b) dry cell weight (c) suspension exopolysaccharide and (d) medium soluble protein during cultivation of *Virgibacillus pantothenticus* MTCC 6729. Symbols represent: ■ Enhanced surface area conico-cylindrical flask (ES-CCF); ● Cylindrical flask (CF); ▲ Erlenmeyer flask (EF). Error bars represent standard deviation of six determinations.

Figure 5:
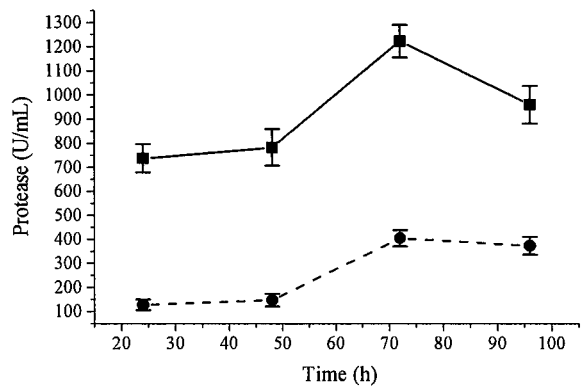
Figure 5:
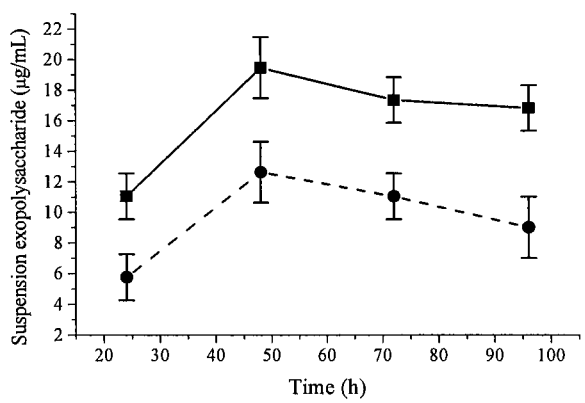
Figure 5:
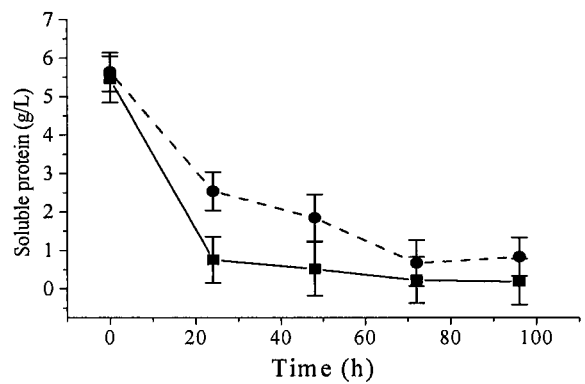

FIG. 5: Effect of glass surface on (a) protease activity, (b) suspension exopolysaccharide and (c) medium soluble protein during cultivation of marine *Pseudomonas* sp. MTCC 8054. Symbols represent: ■ without glass slides; ● glass slides. Error bars represent standard deviation of six determinations.

Figure 6:
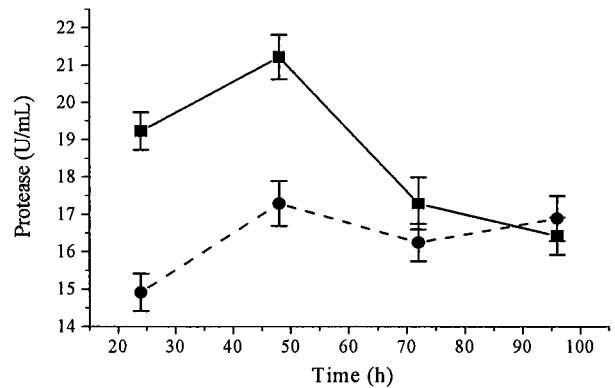
Figure 6:
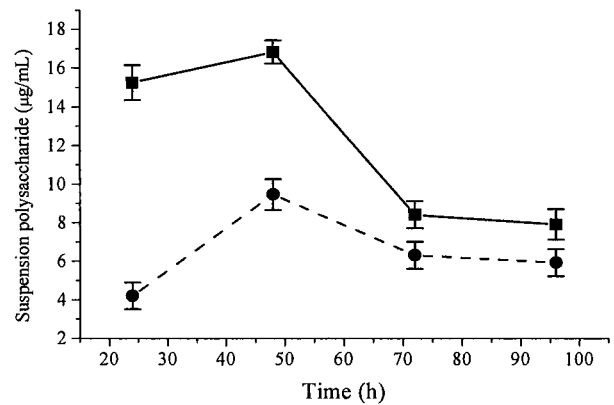
Figure 6:
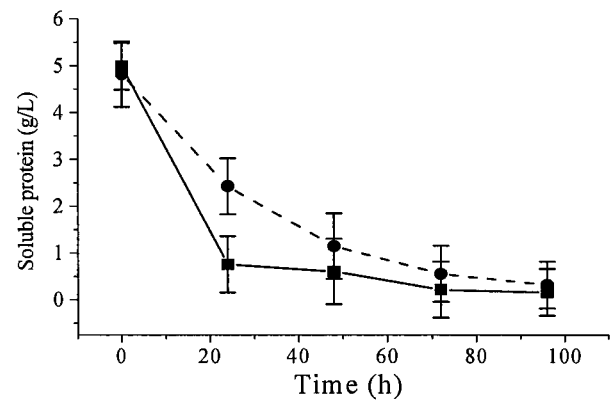

FIG. 6: Effect of glass surface on (a) protease activity, (b) suspension exopolysaccharide and (c) medium soluble protein during cultivation of *Virgibacillus pantothenticus* MTCC 6729. Symbols represent: ■ without glass slides; ● glass slides. Error bars represent standard deviation of six determinations.

DETAILED DESCRIPTION OF THE INVENTION

Accordingly, making reference to FIG. 1a, 1b and FIG. 2a, 2b, the present invention provides the enhanced surface area conico-cylindrical flask (ES-CCF) comprising of three parts namely a lower cylindrical portion, a funnel portion and an inner arrangement. The dimensions are: (a) lower cylindrical portion (height, 150 mm; outer diameter, 80 mm; thickness, 5 mm); (b) funnel portion (diameter of the funnel base, 90 mm; diameter of funnel top, 40 mm). The two parts were joined by screwing the upper part into the lower part. The inner arrangement consists of eight equally spaced rectangular strips mounted on a circular disk (height of the strip, 150 mm; thickness, 5 mm; diameter of the disk, 70 mm; thickness, 5 mm). The surface area of the inner arrangement was 706.4 cm$^2$. The surfaces of the inner arrangement are roughened with Grade 50 sand paper. Ports on the screw cap of the ES-CCF are available for air inlet and exhaust (diameter of ports, 10 mm; diameter of the screw cap, 34 mm).

The novel enhanced surface area conico-cylindrical flask (ES-CCF) provides increased surface area by virtue of its inner arrangement and is useful in routine small-scale studies of bioactive production by any biofilm-forming marine as well as terrestrial microorganisms. Compared to corresponding Erlenmeyer flask of similar volume the ES-CCF provides more than 80% additional surface for biofilm attachment and growth. The device does not require steam sterilization and is durable as it is constructed of polymethylmethacrylate or any other such hydrophobic material and offers possibility of altering the nature of the growth surface on the inner arrangement (hydrophilic and hydrophobic). The present invention also provides external aeration like a bioreactor, thus increasing the versatility of applications. The present invention further provides the device to be operated as a cylindrical flask, that is without the inner arrangement.

The levels of protease production and biofilm formation by marine *Pseudomonas* sp. MTCC 8054 (Sana, B., Ghosh, D., Saha, M., Mukherjee, J., 2006. Purification and characterization of a salt, solvent, detergent and bleach tolerant protease from a new gamma-Proteobacterium isolated from the marine environment of the Sundarbans. Process Biochem. 41, 208-215) and *Virgibacillus pantothenticus* MTCC 6729 (Gupta, A., Joseph, B., Mani, A., Thomas, G., 2008. Biosynthesis and properties of an extracellular thermostable serine alkaline protease from *Virgibacillus pantothenticus*. World J. Microbiol. Biotechnol. 24, 237-243) were studied in the enhanced surface area conico-cylindrical flask (ES-CCF), cylindrical flask (CF) that is the ES-CCF without the inner arrangement and conventional Erlenmeyer flasks (EF). Additionally, protease production was determined in cultures grown in ES-CCFs with a hydrophilic or a hydrophobic surface. The surfaces of the inner arrangement were roughened with Grade 50 sandpaper. For sterilization, the ES-CCF was disassembled, the components washed thoroughly in tap water and immersed in 3% (v/v) sodium hypochlorite for 5 h. The parts were then surface-sterilized under UV light (TUV15W/G15T8, Philips, The Netherlands) in a laminar airflow bench for 30 min. Ports on the screw cap of the ES-CCF were available for air inlet and exhaust. One-hundred milliliters of sterile medium was added to each vessel.

EXAMPLES

The following examples are given by way of illustration of the present invention and therefore should not be construed to limit the scope of the present invention.

Example 1

Effect of Flask Configuration on Protease Production, Cell Growth and Biofilm Formation by a Marine *Pseudomonas* sp. MTCC 8054 and a Terrestrial Isolate (*Virgibacillus pantothenticus* MTCC 6729)

(a) Microorganisms and Media Compositions

Marine *Pseudomonas* sp. MTCC 8054 was maintained on Marine Agar (MA) 2216 medium containing (g/L) peptone, 5; yeast extract, 1; $FeCl_3$, 0.1; $MgCl_2$, 8.8; NaCl, 19.45; $Na_2SO_4$, 3.24; $CaCl_2 \cdot 6H_2O$, 1.8; KCl, 0.55; $NaHCO_3$, 0.16; KBr, 0.08; $SrCl_2$, 0.034; $H_3BO_3$, 0.022; $Na_2SiO_3$, 0.004; NaF, 0.0024; $NH_4NO_3$, 0.0016; $Na_2HPO_4$, 0.008; agar, 15; pH 7.0-7.2. The culture was stored at 4° C. and transferred to fresh medium every month. Marine Broth (MB) 2216 medium supplemented with 120 g/L sucrose (pH adjusted to 6.0 before autoclaving) was used as optimized medium for protease production by marine *Pseudomonas* sp. MTCC 8054. Sucrose was autoclaved separately at 121° C. for 15 min and added aseptically to MB 2216 medium (Atlas, R. M., 2005. Handbook of Media for Environmental Microbiology, Second Ed. Taylor Francis, Boca Raton). The nitrogen content of peptone and yeast extract was determined with a 240C Elemental Analyzer (Perkin Elmer). One percent (v/v) of a 24-h culture was used as inoculums. *V. pantothenticus* MTCC 6729, isolated from chicken meat was cultured in medium comprised of (g/L) sucrose, 5; citric acid, 5; yeast extract, 10; $K_2HPO_4$, 1; $MgSO_4 \cdot 7H_2O$, 0.1 and $CaCl_2 \cdot 2H_2O$, 0.1; pH 9.0. Five percent (v/v) of a 20-h culture was used as inoculums. Cultivation temperatures for marine *Pseudomonas* sp. MTCC 8054 and *V. pantothenticus* were 35 and 40° C., respectively.

(b) Protease Assay and Effect of Flask Configuration on Protease Activity

Protease activity was assayed by using casein as a substrate (Sana et al., 2006). The reaction mixture containing 100 μL Tris-HCl buffer (100 mM, pH 8.5), 100 μL of 1% casein and 200 μL of culture supernatant was incubated at 40° C. (37° C. for *V. pantothenticus* culture supernatant) for 30 min. The reaction was terminated by addition of 400 μL of 10% trichloroacetic acid and the non-hydrolyzed casein was collected by centrifugation at 9300g (Eppendorf Model 5415D, rotor: F45-24-11) for 10 min. For each determination, two sets of control tubes were employed. In the first, 200 μL of culture supernatant and in the second, 100 μL of casein solution was added after the addition of trichloroacetic acid solution. The peptide concentration of the supernatant was determined by measuring absorbance at 280 nm using a Lambda 25 UV/Vis spectrophotometer (Perkin-Elmer) against a blank consisting of 400 μL Tris-HCl buffer and 400 μL 10% trichloroacetic acid and tyrosine as the standard. One unit of proteolytic activity was defined as the amount of the enzyme required to liberate 1 μmol of tyrosine per minute at pH 8.5 and temperature 40° C. (37° C. for *V. pantothenticus* culture supernatant).

FIG. 3a represents the effect of flask configuration on protease production by marine *Pseudomonas* sp. MTCC 8054. Maximum protease activity was obtained in the ES-CCF (1160±16 U/mL at 72 h) compared to the CF (972.5±16 U/mL at 72 h) and EF (895.0±13 U/mL at 48 h). Maximum protease activities from *V. pantothenticus* MTCC 6729 were attained in 48 h (FIG. 4a), though the levels varied depending upon the vessel configuration and were 20.4±0.7 U/mL for ES-CCF, 16.29±0.6 U/mL for CF and 14.9515±0.6 U/mL for EF.

(c) Measurement of Planktonic Growth and Effect of Flask Configuration Thereupon Planktonic cell growth, defined as growth measured from samples withdrawn from suspension and not from the biofilm was determined by recording cell dry weight and viable cell count. Culture samples (1.0 mL) were centrifuged at 9300g (Eppendorf Model 5415D, rotor: F45-24-11) for 5 min. The supernatant was discarded and the cell pellet resuspended in an equal volume of distilled water and recentrifuged. The biomass was dried at 105° C. overnight and weighed. Viable cell growth expressed as colony forming units (CFUs) per mL was determined by plating 100 μL of a suitably diluted culture on MA 2216 medium (for isolate marine *Pseudomonas* sp. MTCC 8054) and nutrient agar (for *V. pantothenticus* MTCC 6729) and incubation at 35-40° C. for 24 h (Sarkar et al., 2010). For both marine *Pseudomonas* sp. MTCC 8054 and *V. pantothenticus* MTCC 6729 planktonic cell growth was higher in the ES-CCF compared to the CF and EF (FIGS. 3b and 4b).

(d) Measurement of Biofilm Formation and Extent of Biofilm Formation in Different Flask Configurations In the experiments related to the effect of flask configuration on protease activity, biofilm formation was quantified by scraping of an area of approximately 45 cm² area of the total surface of the various flask configurations with a sharp scalpel at the end of the experiment and measuring the dry weight on an electronic digital balance (AFCOSET, Model ER-180A, Mumbai, India) as described by Sarkar et al., 2010. For the experiments studying the effect of surface properties on enzyme activity, biofilm formation in the inner arrangement of the ES-CCF was assessed by an attachment assay (Bruhn, J. B., Gram, L., Belas, R., 2007. Production of antibacterial compounds and biofilm formation by *Roseobacter* species are influenced by culture conditions. Appl. Environ. Microbiol. 73, 442-450). Non- and poorly attached bacteria were removed by placing the inner arrangement on a sterile absorbent paper. The inner arrangement was incubated at 60° C. for 30 min, submersed in 0.1% crystal violet for 15 min at room temperature and unbound dye was removed by rinsing with phosphate-buffered saline. The inner arrangement was immersed in 2 mL of 33% acetic acid to solubilize the dye bound to the biofilm, and the absorbance was measured using a spectrophotometer at 590 nm.

For marine *Pseudomonas* sp. MTCC 8054, biofilm formation (as recorded by average weights) was higher in the ES-CCF (0.0118±0.0020 g) compared to the CF (0.0009±0.0001 g) while no biofilm was formed in the EF. For *V. pantothenticus* also biofilm formation was maximum in ES-CCF (0.3729±0.0300 g) compared to CF (0.2603±0.0350 g), while no biofilm was formed in the EF.

(e) Estimation of Exopolysaccharides (EPS) and Effect of Flask Configuration on Suspension and Biofilm EPS Concentration The EPS in suspension was estimated as described by Rodrigues and Bhosle (Rodrigues, C. and Bhosle, N. B., 1991. Exopolysaccharide production by *Vibrio fishceri*, a fouling marine bacterium. Biofouling 4, 301-308) and Saravanan and Jayachandran (Saravanan, P. and Jayachandran, S., 2008. Preliminary characterization of exopolysaccharides produced by a marine biofilm-forming bacterium *Pseudoalteromonas ruthenica* (SBT 033). Lett. Appl. Microbiol. 46, 1-6). To 1 mL of cell-free supernatant, 2 mL of distilled alcohol (90%) was added and incubated for 12 h at −20° C. The EPS was obtained by centrifugation at 8100g (Eppendorf Model 5415D, rotor: F45-24-11) for 15 min. The precipitate was air dried for 4 h and dissolved in 2 mL of distilled water. The polysaccharide content was measured using the anthrone method (Ahimou, F., Semmens, M. J., Haugstad, G., Novak, P. J., 2007. Effect of protein, polysaccharide, and oxygen concentration profiles on biofilm cohesiveness. Appl. Environ. Microbiol. 73, 2905-2910). Glucose was used as standard, and the absorbance was measured at 625 nm to estimate the concentration of hexose sugars.

Biofilm EPS was determined following the method of Ahimou et al. (2007). For polysaccharide quantification, the samples were first dried at 40° C. for 2 h, resuspended in 1 N NaOH and heated at 80° C. for 30 min in a water bath. The samples were centrifuged at 8100g (Eppendorf Model 5415D, rotor: F45-24-11) and 4° C. for 15 min and the polysaccharide concentration was determined in the supernatant. All experiments were performed thrice in duplicate sets and the values reported are the averages of six determinations.

For both marine *Pseudomonas* sp. MTCC 8054 and *V. pantothenticus* MTCC 6729 cell suspension EPS was significantly higher in the ES-CCF (FIGS. 3c and 4c). For marine *Pseudomonas* sp. MTCC 8054, average biofilm EPS values were 75.3±0.5 μg/mL culture and 6.4±0.3 mg of EPS/g of biofilm for the ES-CCF cultivations, while negligible amounts of biofilm EPS were formed in CF and EF cultivations. Similarly for *V. pantothenticus* MTCC 6729 average values of biofilm EPS were also higher in the ES-CCF (342.1±2.0 μg/mL and 917.4±5.0 mg of EPS/g of biofilm) compared to the CF (220.0±5.0 μg/mL and 845.0±5.0 mg of EPS/g of biofilm) while no detectable amount was recorded in the Erlenmeyer flasks.

(f) Determination of Soluble Protein and Utilization of Protein in Different Flask Configurations Soluble protein was measured following the Bradford method as described by Kruger (Kruger, N. J., 1994. Bradford method for protein quantification. In: Walker, J. M. (Ed.), Basic Protein and Peptide Protocols. Springer Verlag, New York, pp. 9-15). The color reagent was prepared by dissolving 100 mg of Coomassie Brilliant Blue G-250 (SRL, Mumbai, India) in 50 mL of 95% ethanol. To this solution, 100 mL of 85% ortho-phosphoric acid (SRL, Mumbai, India) was added. The volume was made up to 1000 mL and filtered through Whatman No. 1 filter paper before use. To 100 μL of appropriately diluted culture supernatant sample, 1000 μL of the prepared reagent was added, mixed thoroughly, and the absorbance was recorded at 595 nm against a distilled water blank. Soluble protein concentration was determined against a calibration curve prepared with bovine serum albumin standard in the range 0-100 μg/mL.

Utilization of soluble protein (FIGS. 3d and 4d) was faster in the ES-CCF than in the CF or EF for both marine *Pseudomonas* sp. MTCC 8054 and *V. pantothenticus* MTCC 6729.

Example 2

Effect of Surface Property of the Inner Arrangement on Protease Production, Cell Growth and Biofilm Formation by a Marine *Pseudomonas* sp. MTCC 8054 and a Terrestrial Isolate (*Virgibacillus pantothenticus* MTCC 6729)

In order to study the effect of surface property of the inner arrangement on enzyme production and biofilm formation sixteen autoclaved borosilicate microscope glass slides (75 mm×25 mm×1.35 mm) were aseptically attached to both sides of the eight-strip inner arrangement of the ES-CCF with a strong non-toxic adhesive (Fevi Kwik, Pidilite Industries Ltd., Mumbai, India). This provided a hydrophilic surface to the inner arrangement of the ES-CCF, while the unmodified ES-CCF made of PMMA had hydrophobic surface characteristics. The glass slides were roughened with Grade 50 sand paper. Quantitative measurement of roughness was obtained for roughened PMMA surfaces of fifteen rectangular strips of the inner arrangement and the same number of roughened microscope glass slides at the start of the experiments and after 16 months at the end of the study. The roughness average value ($R_a$) was determined on a stylus type profilometer (Surtronic 3+, Taylor Hobson Ltd., England). The traverse length was 4.0 mm and the cut-off length was 0.8 mm. A traverse speed of 1 mm/sec and a Gaussian filter were applied. Talyprofile (Taylor Hobson, England) software was employed for data analysis.

The roughness average $R_a$ (PMMA) was estimated as 2.51±0.02 μm while $R_a$ (glass) was determined to be 2.39±0.02 μm. Thus, the two materials were of almost equal roughness. Protease production by isolate marine *Pseudomonas* sp. MTCC 8054 and strain *V. pantothenticus* MTCC 6729 was higher in cultivations where the inner arrangement was without glass slides than when lined with glass slides (FIGS. 5a and 6a). Protease production increased by 202% and growth by 19,275% for marine *Pseudomonas* sp. MTCC 8054 in the presence of a hydrophobic as compared to a hydrophilic surface. Biofilm formation, as determined by attachment assay, was reduced drastically when the glass slides were used ($OD_{590}$=0.357±0.002 for ES-CCF without glass slide and no detectable $OD_{590}$ for ES-CCF with glass slide). Also, the concentration of cell suspension EPS was higher when isolate marine *Pseudomonas* sp. MTCC 8054 was cultivated in the ES-CCF without glass slide lining (FIG. 5b). Suspended cell growth was 100-fold higher (16×10$^7$ CFU/mL with glass and 31×10$^9$ CFU/mL without glass).

For the strain *V. pantothenticus* MTCC 6729 protease production increased by 22% and growth by 940% in the presence of a hydrophobic as compared to a hydrophilic surface. Average biofilm formation was considerably lower when glass slides were used ($OD_{590}$=0.841±0.002 for ES-CCF without glass slide and $OD_{590}$=0.050±0.001 for ES-CCF with glass slide). Suspended cell growth was 10-fold higher (25×10$^8$ CFU/mL with glass and 26×10$^9$ CFU/mL without glass).

Example 3

Effect of Modes of Aeration on Protease Production and Cell Growth by a Marine *Pseudomonas* sp. MTCC 8054 and a Terrestrial Isolate (*Virgibacillus pantothenticus* MTCC 6729)

Three modes of aeration were examined in each of the three (ES-CCF, CF and EF) reactor configurations with the isolate marine *Pseudomonas* sp. MTCC 8054 and *V. pantothenticus* MTCC 6729, shaking at 140 rpm in an orbital shaker (with cotton plugs), orbital shaking with external aeration of 0.75 L/min of air (through ports on top of ES-CCF and CF), and external aeration without shaking (Table 1 and Table 2).

TABLE 1

Maximum protease activity (PA, U/mL) and dry cell weight (DCW, g/mL) of suspension cells for marine *Pseudomonas* sp. MTCC 8054 grown under three modes of aeration, I—shaking at 140 rpm in an orbital shaker (with cotton plugs), II—orbital shaking with external aeration of 0.75 L/min of air and III—external aeration without shaking in three flask configurations, ES-CCF, CF and EF. Data shown in bold indicate highest values obtained with three modes of aeration for marine *Pseudomonas* sp. MTCC 8054.

| | I | | II | | III | |
|---|---|---|---|---|---|---|
| Flask | PA | DCW | PA | DCW | PA | DCW |
| ES-CCF | 1153 ± 17 | 0.042 ± 0.002 | 657 ± 20 | 0.035 ± 0.001 | 214 ± 25 | 0.030 ± 0.002 |
| CF | 912 ± 18 | 0.032 ± 0.002 | 567 ± 21 | 0.030 ± 0.001 | 178 ± 17 | 0.025 ± 0.002 |
| EF | 848 ± 22 | 0.030 ± 0.002 | 523 ± 14 | 0.025 ± 0.001 | 147 ± 18 | 0.025 ± 0.002 |

Of the three modes of aeration considered, orbital shaking at 140 rpm was most favorable for enzyme production and cell growth. Maximum protease activity of 1153±17 U/mL was obtained in the ES-CCF compared to protease activities obtained for the other two configurations i.e. 912±18 U/mL in the CF and 848±22 U/mL in the EF for isolate marine *Pseudomonas* sp. MTCC 8054. For cell growth also maximum dry cell weight of 0.042±0.002 g/mL was obtained in the ES-CCF compared to maximum dry cell weight obtained for the other two configurations i.e. 0.032±0.002 g/mL in the CF and 0.030±0.002 g/mL in the EF.

TABLE 2

Maximum protease activity (PA, U/mL) and dry cell weight (DCW, g/mL) of suspension cells for *Virgibacillus pantothenticus* MTCC 6729 grown under three modes of aeration, I—shaking at 140 rpm in an orbital shaker (with cotton plugs), II—orbital shaking with external aeration of 0.75 L/min of air and III—external aeration without shaking in three flask configurations, ES-CCF, CF and EF. Data shown in bold indicate highest values obtained with three modes of aeration for *Virgibacillus pantothenticus* MTCC 6729.

| | I | | II | | III | |
|---|---|---|---|---|---|---|
| Flask | PA | DCW | PA | DCW | PA | DCW |
| ES-CCF | 21.5 ± 0.5 | 0.32 ± 0.01 | 12.8 ± 0.6 | 0.22 ± 0.01 | 13.7 ± 0.4 | 0.17 ± 0.02 |
| CF | 17.5 ± 0.5 | 0.23 ± 0.01 | 9.8 ± 0.6 | 0.18 ± 0.01 | 8.4 ± 0.4 | 0.16 ± 0.02 |
| EF | 16.3 ± 0.5 | 0.19 ± 0.01 | 8.2 ± 0.6 | 0.15 ± 0.01 | 7.5 ± 0.4 | 0.14 ± 0.02 |

For *Virgibacillus pantothenticus* MTCC 6729, with orbital shaking at 140 rpm, maximum protease activity of 21.50.5 U/mL was obtained in the ES-CCF compared to protease activities obtained in the other two configurations i.e. 17.5±0.5 U/mL for CF and 16.3±0.5 U/mL for EF. As regards cell growth, with orbital shaking at 140 rpm, maximum dry cell weight of 0.32±0.01 g/mL was obtained in the ES-CCF compared to maximum dry cell weight obtained in the other two configurations i.e 0.23±0.01 g/mL for CF and 0.19±0.01 g/mL for EF.

9. Advantages

The Main Advantages of this Device are:
1. Provides enhanced surface area by virtue of its inner arrangement. (Compared to corresponding Erlenmeyer flask of similar volume the ES-CCF provides more than 80% additional surface for biofilm attachment and growth).
2. Allows external aeration like a bioreactor.
3. Has dimensions close to a standard Erlenmeyer flask, hence can be fitted into standard rotary shaker platforms.
4. Offers possibility of altering the nature of the growth surface (hydrophilic and hydrophobic)
5. Constructed of polymethylmethacrylate or any other such hydrophobic material and not glass, hence durable.
6. Can be operated as a cylindrical flask
7. Does not require steam sterilization.
8. Low cost (approx. US$ 50 per unit).

We claim:

1. An enhanced surface area conico-cylindrical flask (ES-CCF) for biofilm cultivation of a biofilm-forming microorganism comprising:
   a funnel portion;
   a lower cylindrical portion being closed at a lower end and open at a upper end with the upper end comprising a middle threading portion for joining the funnel portion and lower cylindrical portion;
   a neck being detachably mounted at a top of the funnel portion;
   a screw cap having two openings each for accepting a port with a first port being an air inlet port and a second port being an exhaust port, the screw cap being detachably fitted onto the neck;
   wherein the lower cylindrical portion accepts an inner arrangement having a plurality of equally spaced rectangular strips directly mounted onto a circular disk;
   wherein the inner arrangement is removably placed inside the lower cylindrical portion with the circular disk positioned at the lower end of the lower cylindrical portion;
   wherein each rectangular strip of the inner arrangement is orientated outward from a central axis and orientated perpendicular to a tangent of the circumference of the lower cylindrical portion;
   wherein a long side of each rectangular strip is parallel to the axis between the lower end and the upper end of the lower cylindrical portion; and
   wherein at least one of the lower cylindrical portion, the rectangular strips of the inner arrangement, and the circular disk of the inner arrangement is made of polymethylmethacrylate (PMMA).

2. The ES-CCF as claimed in claim 1, wherein the lower cylindrical portion and the funnel portion are joined by screwing the funnel portion onto the threading portion of the lower cylindrical portion.

3. The ES-CCF as claimed in claim 1, wherein the two openings in the screw cap allow aeration and exhaustion, respectively, of the interior of the ES-CCF.

4. The ES-CCF as claimed in claim 1, wherein the inner arrangement has hydrophilic or hydrophobic surfaces.

5. The ES-CCF as claimed in claim 1, wherein the ES-CCF is configured to be fitted into a rotary shaker platform.

6. The ES-CCF as claimed in claim 1, wherein the inner arrangement comprises at least eight rectangular strips.

7. The ES-CCF as claimed in claim 1, wherein the height of each rectangular strip of the inner arrangement is substantially identical to the height of the lower cylindrical portion.

8. The ES-CCF as claimed in claim 1, wherein the neck comprises a first threading portion for detachably joining with the top of the funnel portion and a second threading portion for detachably fitting the screw cap.

9. The ES-CCF as claimed in claim 1, wherein at least one of the funnel portion and screw cap is made of polypropylene.

* * * * *

UNITED STATES PATENT AND TRADEMARK OFFICE
CERTIFICATE OF CORRECTION

| | | |
|---|---|---|
| PATENT NO. | : 8,945,917 B2 | Page 1 of 1 |
| APPLICATION NO. | : 13/111022 | |
| DATED | : February 3, 2015 | |
| INVENTOR(S) | : Sreyashi Sarkar et al. | |

It is certified that error appears in the above-identified patent and that said Letters Patent is hereby corrected as shown below:

Title page item (73), change "Council of Scientific & Industrial Research and School of Environmental Studies" to -- Council of Scientific & Industrial Research --

Signed and Sealed this
Eighth Day of December, 2015

Michelle K. Lee
*Director of the United States Patent and Trademark Office*